United States Patent [19]

Young

[11] 4,224,324
[45] Sep. 23, 1980

[54] NITRO-OLEFIN-SUBSTITUTED QUINOXALINE DIOXIDES

[75] Inventor: Vernon V. Young, Terre Haute, Ind.

[73] Assignee: International Minerals and Chemical Corporation, Terre Haute, Ind.

[21] Appl. No.: 40,832

[22] Filed: May 21, 1979

[51] Int. Cl.³ .................. C07D 241/52; A61K 31/495
[52] U.S. Cl. .................................... 424/250; 544/353
[58] Field of Search ........................ 544/353; 424/250

[56] References Cited

U.S. PATENT DOCUMENTS 3,703,515  11/1972  Gum, Jr. ............................. 544/353

Primary Examiner—Mark L. Berch
Attorney, Agent, or Firm—Robert H. Dewey

[57] ABSTRACT

Nitro-olefin-substituted quinoxaline dioxides represented by the formula:

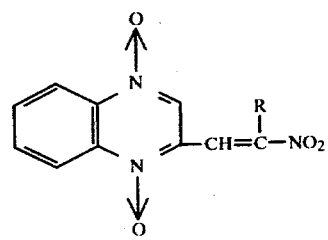

where R is hydrogen or methyl. The compounds are useful for controlling the growth of bacteria and fungi.

6 Claims, No Drawings

NITRO-OLEFIN-SUBSTITUTED QUINOXALINE DIOXIDES

BACKGROUND OF THE INVENTION

This invention relates to a method for controlling the growth of bacteria and fungi. In a particular aspect this invention relates to substituted quinoxaline dioxides.

One of the problems in metalworking industries is the susceptibility of metalworking fluids (which are emulsions of oil or chemical lubricants in water) to microbial attack. Were it not for this microbial contamination, the oil could be used for many months, but actually the microbial growth shortens the working life of the oil considerably. Microbial action may cause the emulsion to break and become acidic, thus causing corrosion problems. Some of the microbes may be pathogenic which can cause skin infections and other industrial health problems. In addition, the microbial mycelia can clog pumps and valves, and often a foul odor develops. In a large installation, frequence replacement of metalworking fluids is costly.

SUMMARY OF THE INVENTION

It is an object of this invention to provide a method for controlling the growth of bacteria and fungi.

It is another object of this invention to provide an antimicrobial composition.

Other objects will be apparent to those skilled in the art from the disclosure herein.

It is the discovery of this invention to provide nitro-olefin-substituted quinoxaline dioxides represented by the formula:

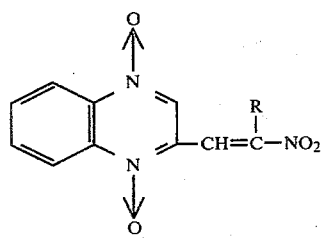

where R is hydrogen or methyl. The compounds are useful for controlling the growth of bacteria and fungi.

DETAILED DISCUSSION

The compounds of the present invention are effective for controlling the growth of a wide variety of microorganisms. They are generally effective to combat the growth of most microorganisms at a concentration of at least about 500 ppm. However, depending on the vigor of the organisms, the length of time during which growth should be suppressed, etc., concentrations of about 1000 ppm or even up to 1500 or 2000 ppm may be preferred.

The compounds of the present invention are prepared by treating the corresponding nitrohydroxy compound with a conventional deacetylating agent, e.g. acetic anhydride or a base such as sodium or potassium carbonate or bicarbonate. Generally an elevated temperature is helpful and it is contemplated that temperatures from ambient up to, e.g., 80°–85° C. are suitable. Preferably a solvent is employed, such as ethyl acetate or glacial acetic acid, or acetic anhydride itself.

The method of controlling the growth of microorganisms of this invention comprises application of an antimicrobial compound represented by the above formula to a substratum infested with the microorganisms to be controlled or to a substratum to be protected from infestation with the microorganisms. The term substratum as used herein is intended to mean the environment or medium upon which an organism grows and includes both animate and inanimate matter, such as animal and vegetable, living or dead, and the soil. The terms microbe and microorganism as used herein are intended to include bacteria and fungi. The term antimicrobial as used herein is intended to include the terms bactericidal, bacteriostatic, fungicidal and fungistatic. No attempt has been made to determine if the products actually cause the death of the organism or merely prevent their growth. The compounds are especially useful in cutting oils for metalworking, latex paints, and recirculated cooling water.

The compounds of this invention are soluble in organic solvents such as aliphatic alcohols and ketones and can be employed as a non-aqueous solution if desired. Also, if preferred, the compounds can be used as such without dilution.

In controlling the growth of microorganisms the combination of this invention is supplied to the organisms or to their environment in a lethal or toxic amount. This can be done by dispersing a compound or mixture thereof, or a composition containing it, in, on or over an environment or substratum infested with, or to be protected from, the microorganisms. A compound of this invention or a mixture containing it can be dispersed in any conventional method which permits contact between the organisms and the antimicrobial agents of this invention. The system to be protected may contain a compound of this invention added by the manufacturer at the time of manufacture or preparation. Alternatively, the proper amount of the compound can be added ad libitum.

The invention will be better understood with reference to the following examples. It is understood that the examples are intended only to illustrate the invention and it is not intended that the invention be limited thereby.

EXAMPLE 1

2-Formylquinoxaline-1,4-dioxide hydrate, 2 g (0.01 mole) was dissolved in 100 ml of warm methanol. Ten drops of triethylamine were added with stirring and 1 g (0.016 mole) of nitromethane was added. The heat source was removed and the reaction mixture was allowed to cool to room temperature. The methanol was removed by evaporation and the residue was recrystallized from water. There was obtained 2-(2-nitro-1-hydroxyethyl)quinoxaline-1,4-dioxide. It was designated P-2231 for convenience.

Two grams of P-2231 prepared as above were dissolved in 10 ml acetic anhydride and 1.0 ml of piperidine. The mixture was stirred for about 24 hours at room temperature. A precipitate, yellow to orange in color, was obtained and isolated. It was insoluble in common laboratory solvents but soluble in acetic acid, from which it was recrystallized; m.p. 204°–205° C., with decomposition. It analyzed as follows:

|  | C | H | N | O |
|---|---|---|---|---|
| Calc., %: | 51.51 | 3.03 | 18.02 | 27.45 |

|          | C     | H    | N·    | O     |
|----------|-------|------|-------|-------|
| Found, %: | 52.54 | 3.26 | 15.96 | 26.31 |

It was identified as 2-(2-nitroethenyl)quinoxaline-1,4-dioxide and was designated P-2278 for convenience.

The antimicrobial properties of P-2278 were determined by the tube dilution method. Media for the bacterial cultures was trypticase soya broth at pH 7.3 prepared as known in the art, and the media for the fungi was Sabouraud broth at pH 5.6, also prepared as known in the art. The inoculum was standardized by the pour plate method for a total viable organism count. The amount of the inoculum per tube was 5 ml at a population of 105 organisms per ml.

The compound was tested for antibacterial and antifungal activity against eight bacteria and four fungi. The results are listed in the following table. They are reported as minimum inhibitory concentration, which is the range between the highest concentration which permits growth and the lowest concentration which prevents growth. They increase exponentially. Because of uncontrollable variables, such as the vigor of the organism, the data are reproducible to about plus or minus one range.

| Antimicrobial Spectra | | |
|---|---|---|
| | Minimum Inhibitory Concentrations, ug/ml | |
| Organism | P-2278 | P-2282 |
| BACTERIA | | |
| Staphylococcus aureus | 500–1000 | 10–50 |
| Streptococcus faecalis | >1000 | 10–50 |
| Streptococcus hemolyticus | >1000 | 10–50 |
| Escherichia coli | 50–100 | 1–10 |
| Pasteurella pseudotuberculosis | 100–500 | 10–50 |
| Pseudomonas aeruginosa | >1000 | 500–1000 |
| Shigella dysenteriae | 500–1000 | 100–500 |
| Mycobacterium ranae | 100–500 | 50–100 |
| FUNGI | | |
| Aspergillus niger | >1000 | 500–1000 |
| Candida albicans | >1000 | 500–1000 |
| Penicillium sp. | 500–1000 | 10–50 |
| Aspergillus fumigatus | 500–1000 | 1000 |

EXAMPLE 2

The experiment of Example 1 was repeated in all essential details except that nitroethane, 1.5 g (0.02 mole) was substituted for nitromethane and it was recrystallized from ethanol. There was obtained 2-(2-nitro-1-hydroxypropyl)quinoxaline-1,4-dioxide, m.p. 206°–208° C. with decomposition. It was designated P-2230 for convenience. P-2230 was dissolved in an excess of warm acetyl chloride. The mixture was heated to boiling for about 30 minutes, then allowed to cool. The solids which separated were isolated by filtration, rinsed with ether and dried. A sample was purified by recrystallization from a mixture of dimethylsulfoxide and methanol (1 g/5 ml/45 ml respectively). There was obtained 2-(1-acetoxy-2-nitropropyl)quinoxaline-1,4-dioxide. It was designated P-2242 for convenience.

P-2242, 1.5 g, was dissolved in 100 ml of ethyl acetate and 0.5 g potassium carbonate was added. The reactants were stirred and the mixture heated to 65° C. for a few minutes. A color change occurred and a precipitate developed. The heat source was removed, the solution was cooled, and the precipitate was isolated. The solids were washed with water to remove residual potassium carbonate. The crude product was recrystallized from acetic acid (10 ml per 1 g). There was obtained 2-(2-nitropropenyl)quinoxaline-1,4-dioxide, m.p. 196°–198° C. It was designated P-2282 for convenience and analyzed as follows:

|          | C     | H    | N     |
|----------|-------|------|-------|
| Calc., %: | 53.44 | 3.67 | 17.00 |
| Found, %: | 53.99 | 3.81 | 15.74 |

I claim:
1. A nitro-olefin-substituted quinoxaline dioxide represented by the formula

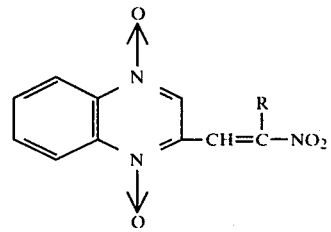

where R is hydrogen or methyl.
2. A compound of claim 1 where R is hydrogen.
3. A compound of claim 1 where R is methyl.
4. A method of controlling the growth of bacteria and fungi by applying to them or to the environment inhabited by them a compound of claim 1.
5. The method of claim 4 wherein R is hydrogen.
6. The method of claim 4 wherein R is methyl.

* * * * *

UNITED STATES PATENT AND TRADEMARK OFFICE
CERTIFICATE OF CORRECTION

PATENT NO. : 4,224,324
DATED : September 23, 1980
INVENTOR(S) : Vernon V. Young

It is certified that error appears in the above-identified patent and that said Letters Patent are hereby corrected as shown below:

Column 1, line 21, "frequence" should read -- frequent --

Column 3, line 16, "105" should read -- $10^5$ --

Signed and Sealed this

Eighteenth Day of August 1981

[SEAL]

Attest:

GERALD J. MOSSINGHOFF

Attesting Officer          Commissioner of Patents and Trademarks